(12) United States Patent
Weber et al.

(10) Patent No.: US 7,618,647 B2
(45) Date of Patent: *Nov. 17, 2009

(54) USING BUCKY PAPER AS A THERAPEUTIC AID IN MEDICAL APPLICATIONS

(75) Inventors: Jan Weber, Maple Grove, MN (US); Tom Holman, Princeton, MN (US); Tracee Eidenschink, Wayzata, MN (US); John Jianhua Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1141 days.

This patent is subject to a terminal disclaimer.

(21) Appl. No.: 10/677,834

(22) Filed: Oct. 3, 2003

(65) Prior Publication Data

US 2005/0074479 A1    Apr. 7, 2005

(51) Int. Cl.
*A61K 2/02* (2006.01)
(52) U.S. Cl. ................................ 424/425; 424/424
(58) Field of Classification Search .................. None
See application file for complete search history.

(56) References Cited

U.S. PATENT DOCUMENTS

| | | | | |
|---|---|---|---|---|
| 6,544,463 B1 * | 4/2003 | Luzzi et al. | .................. | 264/346 |
| 7,037,319 B2 * | 5/2006 | Weber | .................. | 606/192 |

| | | | |
|---|---|---|---|
| 2003/0055407 A1 | 3/2003 | Walik | |

FOREIGN PATENT DOCUMENTS

| | | |
|---|---|---|
| WO | WO 03/026532 A2 | 4/2003 |
| WO | WO 03/092763 A1 | 11/2003 |
| WO | WO 2004/035122 A2 | 4/2004 |
| WO | WO 2004/069169 A2 | 8/2004 |

OTHER PUBLICATIONS

"Fullerene",Wikipedia.com, 2009.*
Baughman et al., "Carbon Nanotubes—the Route Toward Applications," Science, vol. 297, Aug. 2, 2002; pp. 787-792.
Antipov et al., "Sustained Release Properties of Polyelectrolyte Multilayer Capsules," J. Phys. Chem. B 2001, 105, 2281-2284.
Qiu et al., "Studies on the Drug Release Properties of Polysaccharide Multilayers Encapsulated Ibuprofen Microparticles," Langmuir 2001, 17, 5375-5380.
Hird et al., "Supramolecular Structures of Novel Carbohydrate-Based Phospholipids," J. Am. Chem. Soc., 2000, 8097-8098.
Brannon-Peppas, "Polymers in Controlled Drug Delivery," Medical Plastics and Biomaterials Magazine, originally published Nov. 1997.

(Continued)

*Primary Examiner*—Carlos A. Azpuru
(74) *Attorney, Agent, or Firm*—Kenyon & Kenyon LLP

(57) ABSTRACT

Methods, systems, and uses of bucky paper are provided in the present invention. These embodiments include covering medical implants with single or multiple layers of bucky paper, treating bucky paper with various therapeutics to be released through the bucky paper to a target site, shaping bucky paper into non-conventional configurations for improved therapeutic deliver, and using bucky paper alone or in conjunction with other materials to treat a target site.

18 Claims, 7 Drawing Sheets

OTHER PUBLICATIONS

Byrne et al., "Use of Commercial Porous Ceramic Particles for Sustained Drug Delivery," International Journal of Pharmaceutics 246 (2002) 61-73.

Joschek et al., "Chemical and Physicochemical Characterization of Porous Hydroxyapatite Ceramics Made of Natural Bone," Biomaterials 21 (2000) 1645-1658.

Zhang at al., "Crystallization and Microstructure Analysis of Calcium Phosphate-Based Glass Ceramics for Biomedical Applications," Journal of Non-Crystalline Solids 272 (2000) 14-21.

Ausman et al., "Organic Solvent Dispersions of Single-Walled Carbon Nanotubes: Toward Solutions of Pristine Nanotubes," J. Phys. Chem. B, 2000 104, 8911-8915.

Sreekumar, et al., "Single-Wall Carbon Nanotube Films," Chem. Mater. 2003, 15, 175-178.

Spinks et al., "Pneumatic Actuator Response from Carbon Nanotube Sheets," presented on the MRS Fall meeting 2001.

Liu et al., "Fullerene Pipes," Science, 280 (1998), 1253-1256.

Georgakilas et al., "Organic Functionalization of Carbon Nanotubes," J. Am. Chem. Soc. 124 (5) (2002), 760-761.

Chen et al., "Plasma Activation of Carbon Nanotubes for Chemical Modification," J. Phys. Chem. B 2001, 105, 618-622.

Pantarotto et al., "Synthesis, Structural Characterization, and Immunological Properties of Carbon Nanotubes Functionalized with Peptides," J. Am. Chem. Soc. 2003, 125, 6160-6164.

Dettlaff-Weglikowska et al., "Chemical Functionalization of Single Walled Carbon Nanotubes," Current Applied Physics 2 (2002) 497-501.

Bahr et al., "Functionalization of Carbon Nanotubes by Electrochemical Reduction of Aryl Diazonium Salts: A Bucky Paper Electrode," J. Am. Chem. Soc. 2001, 123, 6536-6542.

Chen, et al. "Cyclodextrin-Mediated Soft Cutting of Single-Walled Carbon Nanotubes," J. Am. Chem. Soc. 2001, 123, 6201-6202.

Chen et al., "Solution Properties of Single-Walled Carbon Nanotubes," Science, 1998, 282, 95-98.

Chen et al, "Dissolution of Full-Length Single-Walled Carbon Nanotubes," J. Phys. Chem. B 2001, 105, 2525-2528.

Sun et al., "Soluble Dendron-Functionalized Carbon Nanotubes: Preparation, Characterization, and Properties," Chem. Mater. 2001, 13, 2864-2869.

Bahr et al., "Dissolution of Small Diameter Single-Wall Carbon Nanotubes in Organic Solvents," Chem. Commun. 2001, 193-194.

Wong et al., "Covalently-Functionalized Single-Walled Carbon Nanotube Probe Tips for Chemical Force Microscopy," J. Am. Chem. Soc., 1998, 120, 8557-8558.

Holzinger et al., "Sidewall Functionalization of Carbon Nanotubes," Angew. Chem. Int. Ed., 2001, 40, 4002-4005.

Zhao et al., "Chromatographic Purification and Properties of Soluble Single-Walled Carbon Nanotubes," J. Am. Chem. Soc., 2001, 123, 11673-11677.

Chen et al., "Room-Temperature Assembly of Directional Carbon Nanotube Strings," J. Am. Chem. Soc., 2002, 124, 758-759.

Diehl et al., "Self-Assembled, Deterministic Carbon Nanotube Wiring Networks," Angew Chem. Int. Ed., 2002, 41, 353-356.

Krasheninnikov et al., "Ion-Irradiation-Induced Welding of Carbon Nanotubes," Physical Review B 66, 245403 (2002).

Fisher et al., "Carbon Nanotubes Literature Review," Department of Mechanical Engineering, Northwestern University, Feb. 21, 2001.

Final Report, Nanotechnology Workshop: From the Laboratory to New Commercial Frontiers, Rice University, Houston, Texas, May 23, 2002.

Henry, "Special Delivery—Alternative Methods for Delivering Drugs Improve Performance, Convenience, and Patient Compliance," Chemical & Engineering News, vol. 78, No. 38, Sep. 18, 2000, pp. 49-65.

"Antibody Coated Stent A Breakthrough in Cardiovascular Treatment," ScienceDaily New Release, May 22, 2003.

Klein-Soyer et al., "CD9 Participates in Endothelial Cell Migration During In Vitro Wound Repair," Arterioscler Thromb Vasc Biol., Feb. 2000, pp. 360-369 (http://www.atvbaha.org).

Leng T, et al., "Carbon Nanotub Bucky Paper as an Artificial Support Membrane and Bruch's Membrane Patch in Subretianal RPE and IPE Transplantation", Annual Meeting of the Association for Research in Vision and Ophthalmology, May 4, 2003, E-Abstrat 481, 2 pages.

Wang K, et al., "Carbon Nanotubes as Microelectrodes for a Retinal Prosthesis", Annual Meeting of the Association for Research in Vision and Ophthalmology, May 4, 2003, 2 pages.

Hirsch, A, "Functionalization of Single-Walled Carbon Nanotubes", Angewandte Chemie International Edition, vol. 41, No. 11, 2002, pp. 1853-1859.

\* cited by examiner

STEP 1

STEP 2

STEP 3

USING BUCKY PAPER AS A THERAPEUTIC AID IN MEDICAL APPLICATIONS

FIELD OF THE INVENTION

The present invention is directed to using bucky paper as a remedial aid in medical applications. More specifically, the present invention regards using carbon nanotube bucky paper to facilitate acceptance of a medical implant at a target site, to facilitate healing at a target site or to deliver therapeutic to a target site. In each case, the target site may be within the body of a patient or elsewhere.

BACKGROUND

Carbon nanotubes are single wall or multi-wall carbon structures with diameters that can typically range from 1.4 nm to 15 nm and lengths that can range from 30 nm to 20 centimeters. Nanotubes can behave like metals or semiconductors, can conduct electricity better than copper, can transmit heat better than diamond, and rank among the strongest materials known. Bucky paper is an entangled mat of carbon nanotubes. Being made of carbon, bucky paper is bio-compatible. The carbon nanotubes that comprise the bucky paper form a highly-porous mesh structure that provides the bucky paper with moderate rigidity and high strength.

The delivery of therapeutic via the placement of an implant at a target site inside a patient is an often repeated medical procedure. The benefits and purposes of performing such a procedure are innumerable and can include enlarging constricted lumens, reinforcing recently re-enlarged lumens, replacing ruptured vessels, and targeting the delivery of therapeutic to a specific target site. Implants used in these procedures can be delivered through various methods and systems including balloon angioplasty and catheter injection.

The vessels, lumens, and other target sites, which can be treated by implants alone or implants in combination with therapeutics, can be located throughout the body and can include the coronary vasculature, the esophagus, the trachea, the colon, the biliary tract, the urinary tract, the prostate, the brain, and the various other organs. Examples of implants that have been used include: vena cava filters; stents; stent-grafts; vascular grafts; intraluminal paving systems; pace makers; venous valves; and, heart valves.

BRIEF DESCRIPTION

Methods, systems, and uses of bucky paper are provided in the various embodiments of the present invention. These embodiments include covering medical implants with single or multiple layers of bucky paper, treating bucky paper with various therapeutics to be released through the bucky paper to a target site, shaping bucky paper into non-conventional configurations for improved therapeutic delivery, and using bucky paper alone or in conjunction with other materials to treat a target site.

DETAILED DESCRIPTION

Bucky paper, as used herein, includes mats or meshes of single wall, multi-wall, Y-branched, and coiled carbon nanotubes. These mats or meshes may be manufactured through various methods and means including those described below. The carbon nanotubes that comprise the bucky paper may be open ended nanotubes, closed ended nanotubes, and variants thereof.

Figure 1:
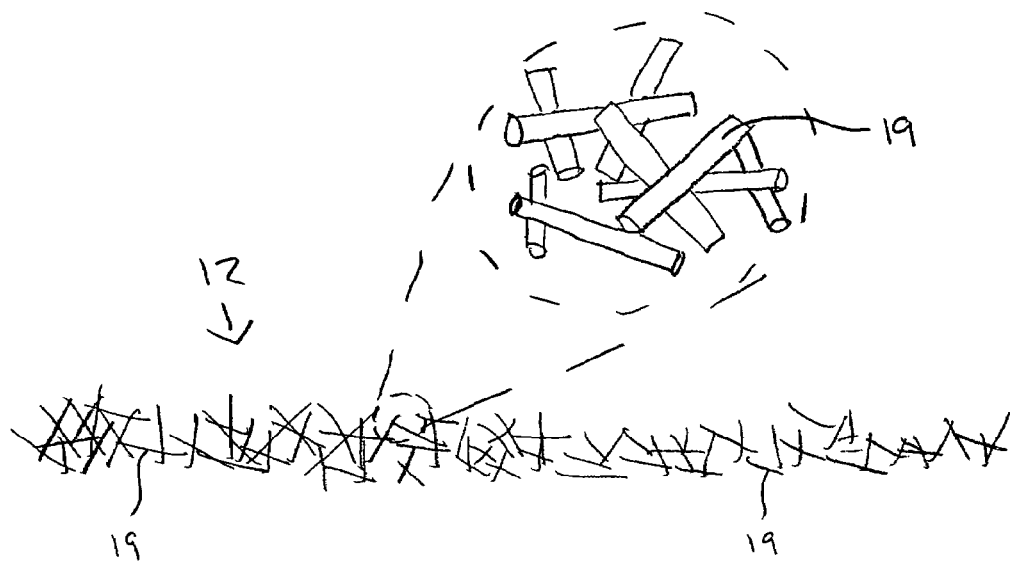
FIG. 1 is a side and enlarged view of bucky paper as may be employed in various embodiments of the present invention.

FIG. 1 is a side view of an exemplary bucky paper 12 as may be used in accord with the various embodiments of the present invention. In FIG. 1, the carbon nanotubes 19 of the bucky paper 12 can be clearly seen in both the regular side view and the enlarged view provided therein. As is visible, the numerous carbon nanotubes 19 comprising the bucky paper may be intermingled amongst themselves and may be oriented in various positions. The unstructured orientation of the carbon nanotubes provides for an irregular exterior surface of the bucky paper. The unstructured orientation of the carbon nanotubes 19 also defines voids and interstices throughout the bucky paper 19. These voids and interstices vary in size and may allow materials smaller than the spaces they create to pass through the bucky paper. Moreover, while the bucky paper 19 is shown in a planar orientation, it may be formed in a curve or other orientation as described below. The bucky paper may be made in various shapes and sizes including polygons of uniform or varying thicknesses. By changing the thickness, shape or density of the bucky paper alone or in combination, its rigidity and flexibility may be modified.

Figure 2:
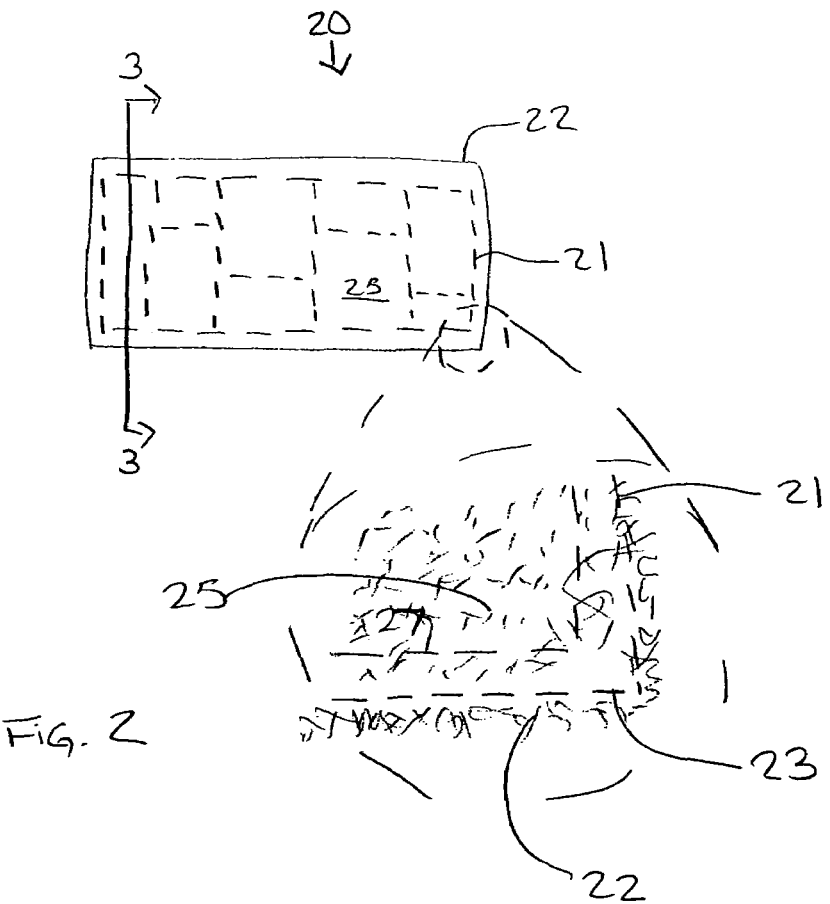
FIG. 2 is a side and enlarged view of a stent covered with bucky paper in accord with an embodiment of the present invention.

FIG. 2 is a side and enlarged view of a stent 20 that has been covered with bucky paper 22 in accord with an embodiment of the present invention. In FIG. 2, the stent 20 is comprised of numerous stent struts 21. These stent struts 21 have an outer face 23 that points outwardly from the stent 20. The stent struts 21 in this embodiment have been covered with bucky paper 22. The bucky paper 22 in this embodiment extends past both ends of the stent and covers not only the stent struts 21 but also the spaces 25 between the stent struts 21. The stent 20 in this embodiment may also be dip or spray coated with a coating prior to or after the bucky paper is adhered to the stent. Furthermore, in an alternative embodiment, rather than covering the spaces 25, the bucky paper may be removed or cut away to leave open areas between the stent struts 21. Still further, only a portion of the stent 20 or other medical device may be covered with bucky paper.

As a result of covering the stent 20 with the bucky paper 22, when the stent 20 is placed at a target site, such as a lumen within the body, the bucky paper 22 may prevent the covered portions of the stent 20 from coming in direct contact with the target site. Thus, if the medical implant were made of metal or some other material, its adaptability to the target site and the probability of acceptance by the target site can be improved by covering the exposed surfaces of the implant with bucky paper.

The bucky paper 22 in this embodiment may be coupled to the stent 20 and its struts 21 through various methods and techniques. These techniques, some of which are described in greater detail below, may include, mechanically attaching the bucky paper to the stent 20 (e.g., clamping, sewing), gluing the bucky paper 22 to the stent 20, forming the bucky paper 22 around the stent 20, and directly depositing the bucky paper 22 onto the stent 20. During some of these forming techniques, the bucky paper 22 will not only be positioned on the stent strut face 23 but may, also, be positioned on other surfaces of the stent strut.

The clamping technique mentioned above could include wrapping the stent 20 with a layer or layers of bucky paper 22 and then using clamps to connect the bucky paper 22 to the stent 20. These clamps could include metallic and non-metallic wires, strands of carbon wire, and other fasteners. Furthermore, instead of clamping the layer or layers of bucky paper 22 to the stent 20 or other medical device being wrapped by the bucky paper 22, the bucky paper 22 may also be sewn to the stent 20, another medical device or even directly onto the target site. Moreover, metallic and non-metallic wires or strands may be used to sew the bucky paper to the stent 20. Still further, glue may also be used to attach the layer or layers of bucky paper 22 to the stent 20. Glues that may be used include cyanoacrylates, polyurethanes, and UV curable glues.

Still further, in another alternative embodiment, rather than sewing or clamping the bucky paper 22 to a medical device, it may, instead, be directly attached to the target site. In other words, during a medical procedure, the medical practitioner may directly sew or clamp one or more layers of bucky paper 22 to the target site. This may be done to shield the target site from a medical implant that will be placed there at a later time, as well as for various other reasons. Moreover, in another alternative embodiment, the bucky paper may be clamped between the device and the vessel wall.

As discussed in greater detail below, in various alternative embodiments of the present invention, therapeutic may be coupled to the bucky paper, may be placed between layers of the bucky paper, and may by placed behind the bucky paper between it and the medical device that the bucky paper covers. In so doing, therapeutic may be delivered to a target site immediately upon the positioning of the bucky paper at the target site, over a period of time or some combination of the two. In an alternative embodiment, and as described below, when layers of bucky paper are clamped to the various cells of the stent 20, nanoparticles or micellae carrying Taxol or other therapeutics may be placed between the layers of the bucky paper in order to deliver the Taxol or other therapeutic to the target site.

Preferred medical devices for use in conjunction with the present invention include catheters, vascular catheters, balloon catheters, guide wires, balloons, filters (e.g., vena cava filters and distal protection filters), vascular stents (including covered stents such as PTFE (polytetrafluoro-ethylene)-covered stents), stent grafts, cerebral stents, cerebral aneurysm filler coils (including GDC (Guglielmi detachable coils) and metal coils), vascular grafts, myocardial plugs, pacemakers, pacemaker leads, heart valves and intraluminal paving systems, filterwires, venous valves, bifurcation stents, aortic stents and, in essence, all devices that can be utilized in the vascular system or the prostate urinary tract bile duct.

Figure 3:
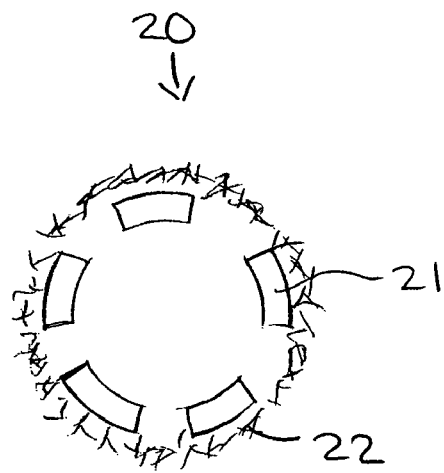
FIG. 3 is a cross-sectional view taken along line 3-3 of FIG. 2.

FIG. 3 is a cross-section taken along line 3-3 of FIG. 2. As can be seen in FIG. 3, the stent 20 of FIG. 2 has struts 21 that form a circular cross-section. As can also be seen, the bucky paper 22 not only covers these struts 21 but also spans the spaces between them. As discussed above, while only one layer of bucky paper 22 is provided in FIG. 3, several layers may be employed. Moreover, the bucky paper 22 may also be placed on the inside of the stent 20 as well. Still further, the stent may also be coated with an additional coating in an alternative embodiment. This coating may be between the bucky paper and the device and may be over the bucky paper and the device.

Figure 4:
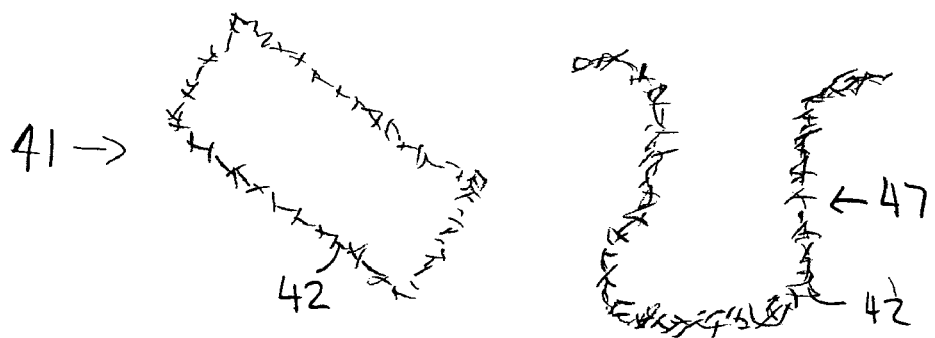
FIG. 4 is side views of bucky paper shaped in the form of a tube and a sack, both in accord with alternative embodiments of the present invention.

FIG. 4 provides alternative embodiments of the present invention. As can be seen (and as mentioned above), bucky paper 42 has been formed in the shape of a cylinder 41 and the shape of a pouch 47. Accordingly, in alternative embodiments, the bucky paper 42 may be shaped in non-planar configurations. This may be done to adapt and contour the bucky paper to the target site, where the bucky paper will be positioned, as well as for other reasons. For instance, if the bucky paper 42 is formed in the shape of a sack or pouch 47, the pouch 47 may be used to surround a targeted pouch like area such as artificial bones or the heart.

The bucky paper may be used in conjunction with other materials, such as silicone rubber. For instance, the silicone rubber may be sandwiched between two layers of bucky paper to form a pouch, a cylinder, or other desired shape. If the bucky paper 42 is formed in the shape of a cylinder 41, it may be implanted in a cylindrical lumen.

In these embodiments, therapeutic may be delivered to the target site directly upon the placement of the bucky paper 42, over time, through time-release from the bucky paper 42, and by using the bucky paper 42 as a lure to alternatively delivered therapeutic. When used as a lure, the bucky paper 42 may be treated before hand by placing magnetized threads in the paper that may then be used to attract para-magnetic or ferromagnetic microparticles containing or otherwise associated with therapeutic.

Figure 5:
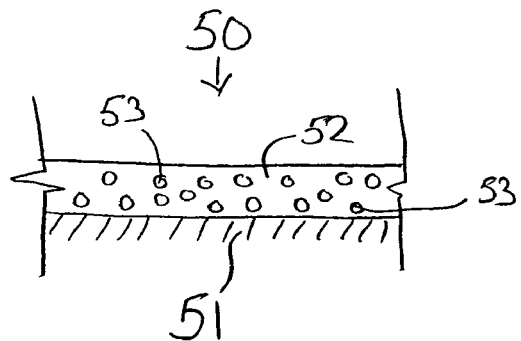
FIG. 5 is a side view of an implant covered with bucky paper in accord with an alternative embodiment of the present invention.

FIG. 5 is a cross-section of a wall 51 of an implant system 50 in accord with another alternative embodiment of the present invention. In this embodiment, the implant 50 is covered with bucky paper 52. The bucky paper 52 contains a therapeutic 53 and is in direct contact with the implant wall 51. The therapeutics that may be used in this embodiment and others are numerous and include pharmaceutically active compounds, nucleic acids with and without carrier vectors such as lipids, compacting agents (such as histones), viruses (such as adenovirus, adenoassociated virus, retrovirus, lentivirus and a-virus), polymers, hyaluronic acid, proteins, cells and the like, with or without targeting sequences.

Other examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application.

Non-limiting examples of virus vectors or vectors derived from viral sources include adenoviral vectors, herpes simplex vectors, papilloma vectors, adeno-associated vectors, retroviral vectors, and the like.

Non-limiting examples of biologically active solutes include anti-thrombogenic agents such as heparin, heparin derivatives, urokinase, and PPACK (dextrophenylalanine proline arginine chioromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/antimitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, antibodies recognizing receptors on endothelial progenitor cells, proteins of the tetraspanin family, such as CD9 Beta-1 and Beta-3 integrins, CD63, CD81, FcgammaRll, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Bucky paper is a hydrophobic substance. Consequently, when hydrophobic agents, such as placitaxel, are used as therapeutics, a simple solution to treat the bucky paper with the therapeutic would be to dip the bucky paper (and the device, if the bucky paper is coupled to a medical device) in a solution containing the therapeutic agent. Now carried by the bucky paper, the therapeutic may be partially or completely released from it when the bucky paper is positioned at a target site.

Comparatively, when hydrophylic therapeutics are used, they may first be encapsulated in liposomes or polysaccharides that are subsequently embedded into the bucky paper. Alternatively, the hydronhilic therapeutics may be crystallized or frozen and then placed within the bucky paper. Still further, microtubes, loaded with therapeutics, may also be embedded in the bucky paper for subsequent release and delivery.

Figure 6:
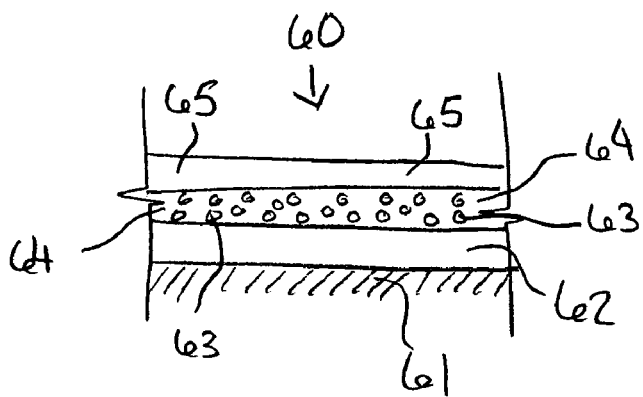
FIG. 6 is a side view of an implant covered with bucky paper in accord with an alternative embodiment of the present invention.

FIG. 6 is a side cross-section of an implant system 60 in accord with another alternative embodiment of the present invention. In the embodiment of FIG. 6 an implant 61 is covered with a first layer of bucky paper 62, a therapeutic carrier 64, and a second layer of bucky paper 65. The therapeutic carrier 64 in this embodiment contains a therapeutic 63. The therapeutic coating or carrier 64 may be used to regulate the release of the therapeutic 63 from the implant system, and to prevent or reduce the burst phenomenon associated with therapeutic delivery. It may also be used to adhere the second layer of bucky paper 65 on the implant 61. Furthermore, if the therapeutic is a biologically active material, it may be permanently resident within the carrier 64 and not released by the carrier.

This implant system 60 may be manufactured by assembling the layers directly on the medical device. These layers may also be assembled elsewhere and then transferred onto the implant already layered together. Alternatively, the two bucky paper layers may be placed on the medical implant 61 with the carrier 64 and therapeutic 63 being injected into the space between them at a later time.

Figure 7:
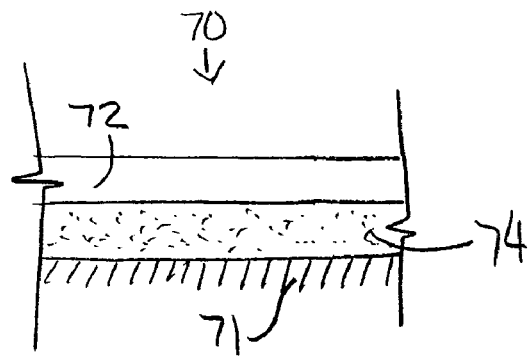
FIG. 7 is a side view of an implant covered with bucky paper in accord with an alternative embodiment of the present invention.

FIG. 7 is a side view of an alternative embodiment of the present invention. In FIG. 7, the implant system 70 includes an implant 71, a therapeutic coating 74 positioned on top of the implant 71, and bucky paper 72 positioned on top of the therapeutic coating 74. Here, the therapeutic coating 74 is positioned directly on top of the implant 71.

Coatings used with the present invention may comprise various polymeric material/drug agent matrices, i.e. gel/drug combinations. These may be formed, for example, by admixing a drug agent with a liquid polymer, in the absence of a solvent, to form a liquid polymer/drug agent mixture. Curing of the mixture in these embodiments may occur in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation, such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. The polymers described herein, which may be formulated as a liquid, may be used to form the polymer/drug agent mixture.

In a preferred embodiment, the polymer used to coat the medical device may be provided in the form of a coating on an expandable portion of the medical device. After applying the drug solution to the polymer and evaporating the volatile solvent from the polymer, the medical device, covered by the polymer and bucky paper, may be inserted into a body lumen and positioned at a target location. In the case of a balloon catheter, the expandable portion of the catheter may be subsequently expanded to bring the drug-impregnated implant system into contact with the lumen wall. The therapeutic may then be released from the polymer as the polymer slowly dissolves in the aqueous bodily fluids or as the therapeutic diffuses out of the polymer. This enables administration of the drug to be site-specific, limiting the exposure of the rest of the body to the therapeutic.

The stent used in the present invention for the coatings or carriers is preferably capable of absorbing a substantial amount of therapeutic solution. When applied as a coating on a medical device in accord with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2-0.3 microns and much thicker coatings, e.g., more than 10 microns, are also possible. It is also within the scope of the present invention to apply multiple layers of polymer coating in addition to multiple layers of bucky paper onto a medical device. Such multiple layers may be the same or different polymer materials. Furthermore, using polyelectrolytes (layer by layer compositions) the polymer layer thickness may be reduced by encapsulating the therapeutic agent in between the polymer layers. These layers may be on the order of 5-50 nanometers.

The carriers and coatings used in the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable, and biostable polymers and copolymers. Coatings from polymer dispersions such as polyurethane dispersions (BAYHYDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205. U.S. Pat No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

Figure 8:
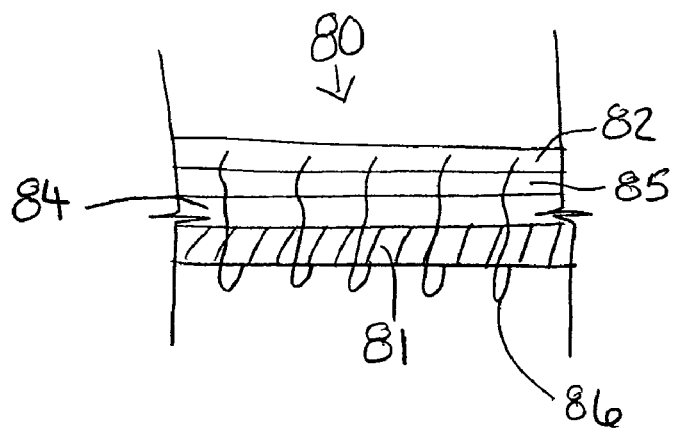
FIG. 8 is a side view of an implant covered with bucky paper in accord with an alternative embodiment of the present invention.

FIG. 8 is a cross-section of another alternative embodiment of the present invention. The implant system 80 of FIG. 8 contains an implant 81, therapeutic coating 84, a delivery barrier 85, and PB anchors 86. The barrier may be made from a biodegradable layer like poly vinyl alcohol or PLLA or a polysaccharide or another multi-layer polyelectrolyte composition. It could also be made from a stable porous polymer like a polyurethane or SIBS. The PE anchors 86 may be formed directly into the bucky paper 82 and may protrude from it. The PE anchors 86 may be used, as is shown in FIG. 8, to secure the bucky paper 82, through the therapeutic coating 84, to the medical implant 81. This securement may be done by melting the PE anchors. In addition to using the coating 84 to control the release of therapeutic from the implant system 81, the delivery barrier 85 may also be used to perform this function. This delivery barrier 85 may be comprised of materials that affect the delivery of the therapeutic in the coating 84. Alternatively, the barrier 85 may simply dissolve over time, thereby providing for the release of therapeutic from the medical implant once the barrier dissolves. The PB anchors 86 formed in the bucky paper 82 of this embodiment may also be used, in alternative embodiments, to attach the bucky paper 82 directly to the target site or to other bucky paper in order to form layers of bucky paper. the bucky paper 82 of this embodiment may also be used, in alternative embodiments, to attach the bucky paper 82 directly to the target site or to other bucky paper in order to form layers of bucky paper.

In another alternative embodiment of the present invention, the implant system 80 may contain an implant 81 with a therapeutic coating within a carrier layer (e.g., styrene-isobutylene-styrene) and a barrier layer, wherein the barrier layer may be bucky paper. The barrier layer may be further improved by associating it with endothelial growth stimulating substances like Heparin as described below.

Figure 9:
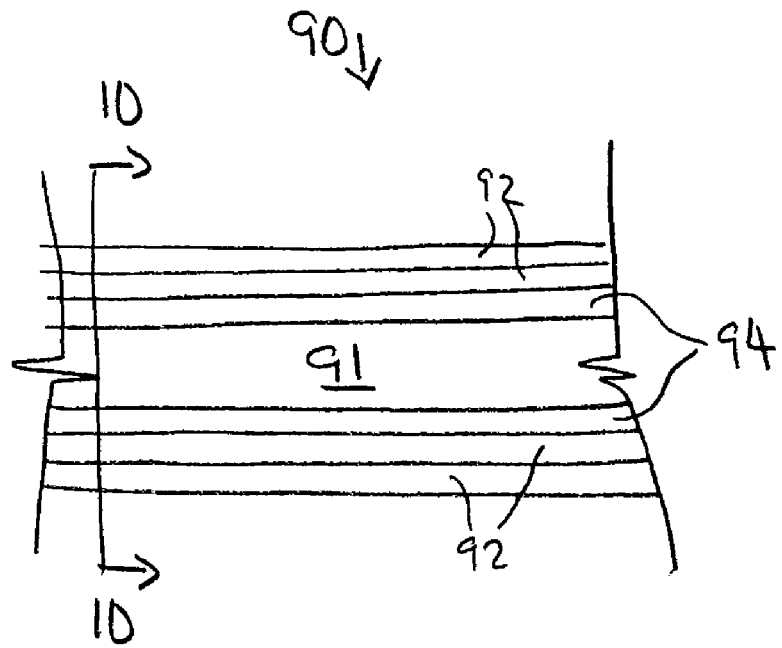
FIG. 9 is a side view of an implant covered with bucky paper in accord with an alternative embodiment of the present invention.

FIG. 9 is an alternative embodiment of the present invention. In FIG. 9, the implant system 90 includes layers of bucky paper 92 positioned on the inside and outside surfaces of the implant strut 91. These layers of bucky paper 92 are positioned on top of therapeutic layers 94. In this embodiment, the outer most bucky paper layer may be untreated while the inner layer of bucky paper may be treated. This treatment can include a plasma process to create chemical anchors such as hydrophilic and carboxylic groups to which one can attach therapeutics.

Figure 10:
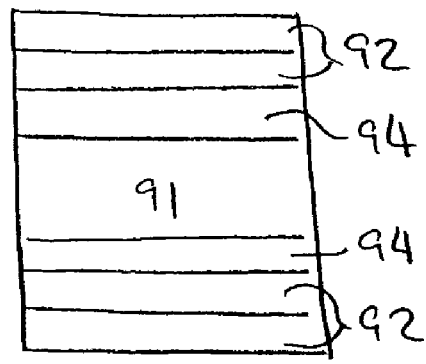
FIG. 10 is a cross-sectional view taken along line 10-10 of FIG. 9.

FIG. 10 is a cross-section along line 10-10 of FIG. 9. As can be seen in FIG. 10, the layers of bucky paper 92 and the therapeutic carrier 94 do not cover all sides of the implant strut 91. Rather, the bucky paper 92 and the therapeutic carrier cover the inside and outside facing surfaces of the strut 91. In alternative embodiments, the bucky paper and the carrier may, instead, cover the entire surface of the implant's struts.

Figure 11:
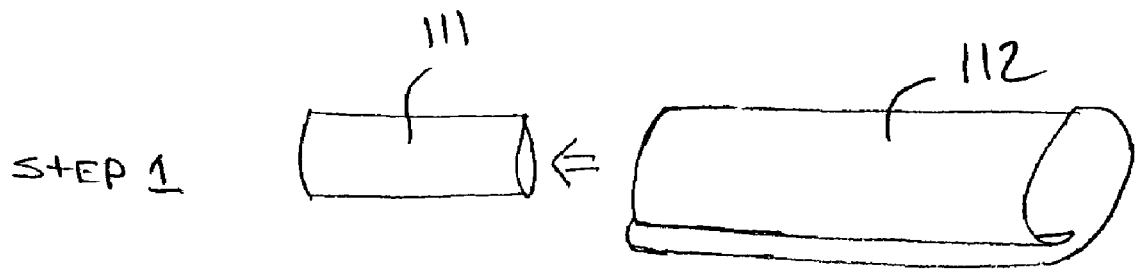
FIG. 11 is a process used to cover a stent with bucky paper in accord with an alternative embodiment of the present invention.
Figure 11:
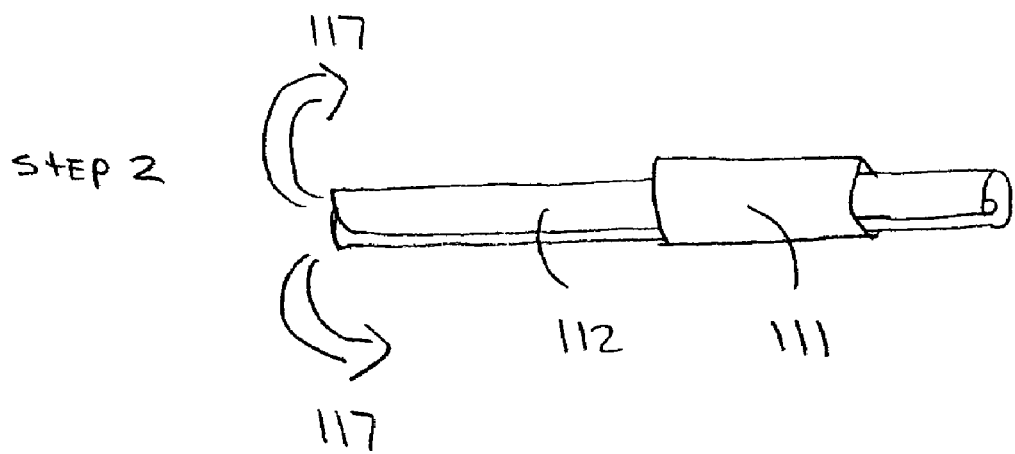
Figure 11:
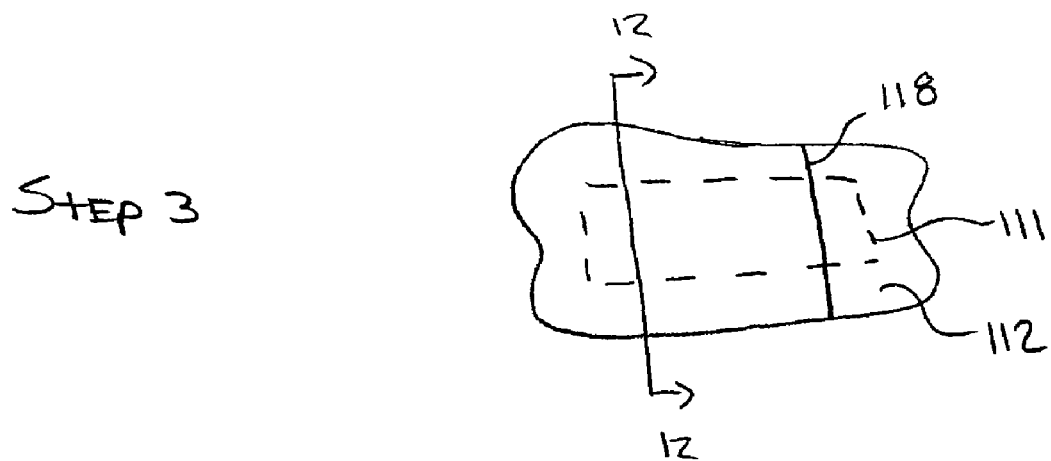

FIG. 11 is an alternative embodiment of the present invention regarding the placement of bucky paper around a medical implant. In this embodiment rolled bucky paper 112 is inserted into a stent 111 (step 1) and then folded back over the stent 111 (step 2) in order to cover the stent 111 with the bucky paper 112. The covered stent 111 is shown in step 3. Also visible in step 3 is the fold line 118, the stent 111, and the bucky paper 112. Alternatively, the paper may first be folded and rolled only once, without an overlap, the stent being placed in the space between.

Figure 12:
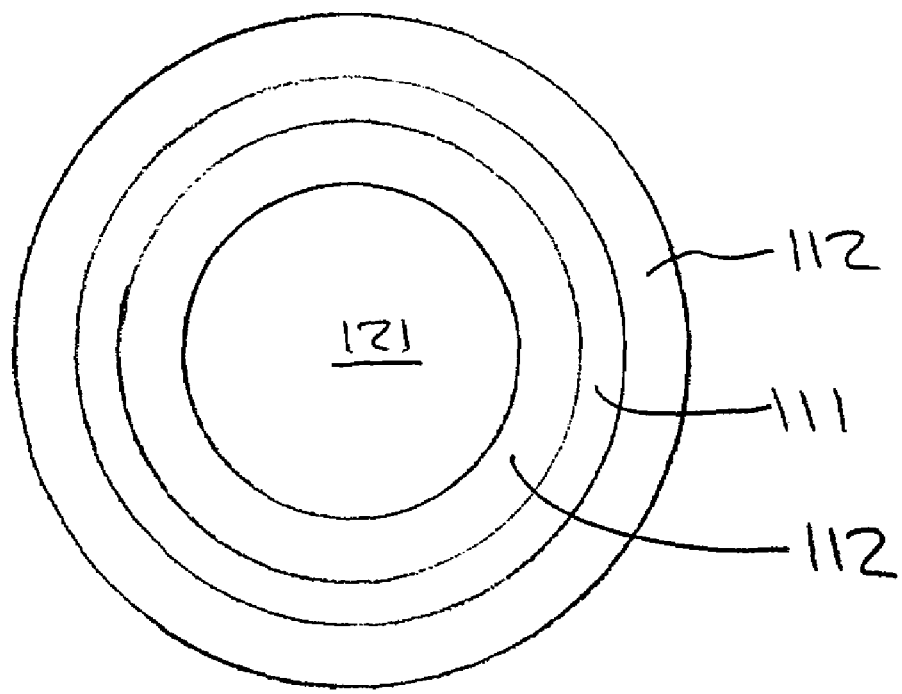
FIG. 12 is a cross-sectional view taken along line 12-12 of FIG. 11.

FIG. 12 is a cross-section taken along line 12-12 of FIG. 11. The bucky paper 112 can be clearly seen on both the inside and the outside surface of the stent 111. The internal passage 121, which is formed by the inner surfaces of the bucky paper 112, can also be seen in this sectional view.

Figure 13:
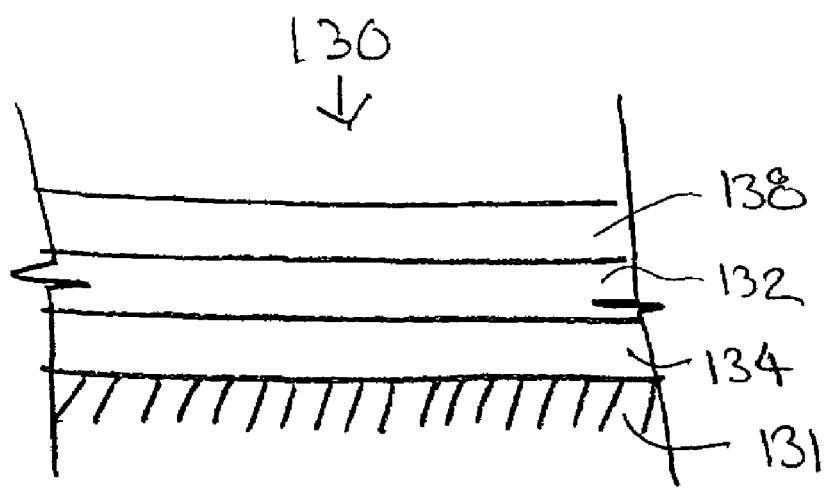
FIG. 13 is a side view of an implant covered with bucky paper in accord with an alternative embodiment of the present invention.

FIG. 13 is a sectional view of an implant system 130 in accord with an alternative embodiment of the present invention. In this embodiment, a release control coating 138 has been placed on top of the bucky paper 132, which is in turn positioned on top of a therapeutic carrier 134. This carrier 134 may include microtubes, ceramic nano-particles, and liposome microparticles. Furthermore, the therapeutic may be encapsulated in biodegradable nano- or microparticles by using poly-electrolyte multilayers. These particles may be designed to open up upon exposure to different phs, changes in osmotic pressure, and changes in external pressure, heat or light.

Bucky paper may be manufactured in one embodiment from commercially obtained SWNT suspensions (Triton X-100 or toluene solution) that have been vacuum filtered to allow for free standing films of highly entangled nanotube ropes. In one embodiment, the bucky paper may be made by vacuum filtering approximately 4 g of approximately 0.6 mg/ml of previously diluted (~80 ml de-ionized $H_2O$) nanotube solution. The filter may be a (Millipore LS, 47 mm in diameter or Whatman Anodisc 47 filter 20 mm pore site) polytetrafluoroethylene filter.

Once created, the filtered mat may then be washed with 200 ml of de-ionized water and 100 ml of methanol. A drying vacuum and heat (70° C.) may be applied for 12 hours. These steps were found to produce bucky paper having a thickness ranging from 13-33 nanometers and a density of 0.3 to 0.4 $g/cm^3$.

These nanotubes may be chemically modified by reacting them with sulfuric and nitric acid. Moreover, hydrophylic and carboxylic groups may be created on the surface of the nanotubes and may be used to bind heparin and albumin molecules to the surface of the nanotubes, which may promote endothelial cell seeding. Plasma may also be used to change the properties of the nanotubes in order to couple various biologically active molecules to them. When these modified nanotubes have been created they may be mixed with untreated nanotubes.

Figure 14:
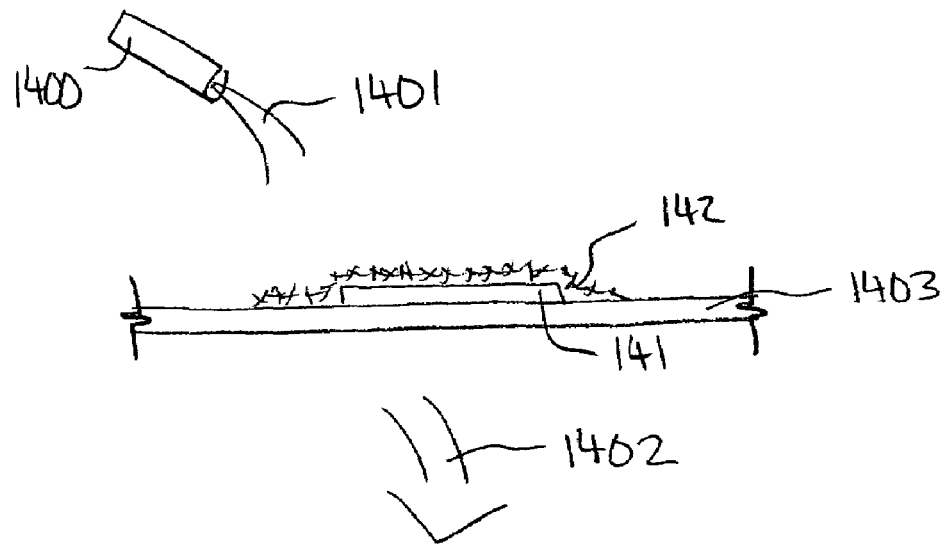
FIG. 14 is a process used to cover an implant in accord with an alternative embodiment of the present invention.

FIG. 14 regards a process that may be used in accord with another alternative embodiment of the present invention. In FIG. 14, a container of single wall nanotubes in solution 1401 is poured onto an implant 141 that has been placed on top of a filter 1403. The filter 1403 is sized to allow the suspending solution to pass through it but to trap the SWNT on top of it. As a result, bucky paper is formed on top of the filter 1403 and on top of the implant 141.

Alternatively, rather than form the bucky paper on a flat filter surface, it may be formed on a cylindrical or tubular filter. Suction or centrifugal forces may be used to create the bucky paper on the filter or to facilitate its drying. Still further, as described above, the filter may be formed in the shape of a bag in order to form the pouch shaped bucky papers described above. Moreover, once the bucky paper is configured, an implant may be placed adjacent to it and additional bucky paper may be formed on top of it to completely encircle the implant.

Figure 15:
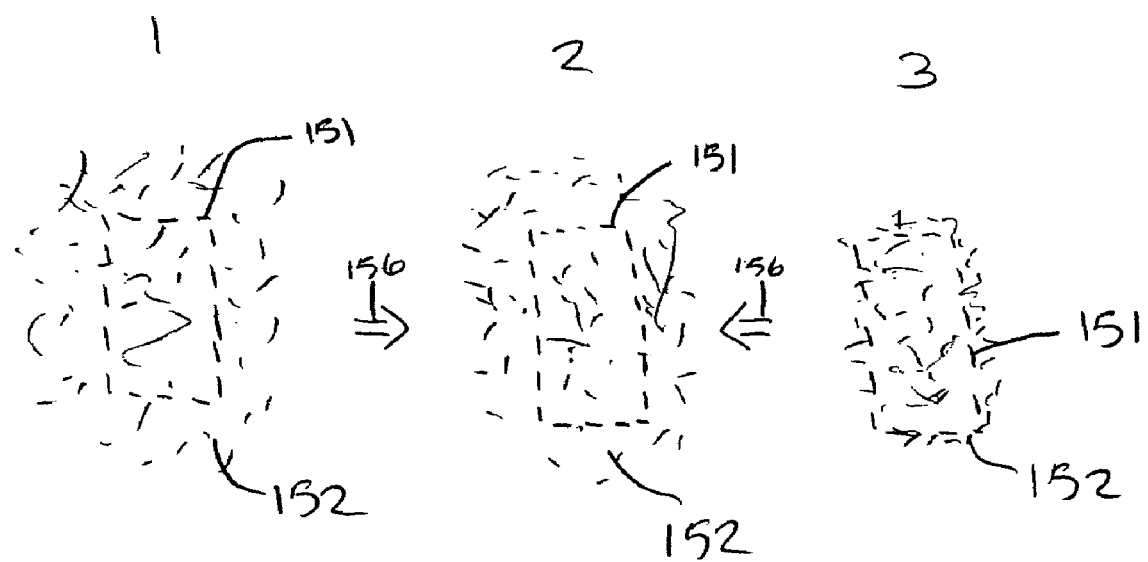
FIG. 15 is a process used to cover an implant in accord with an alternative embodiment of the present invention.

FIG. 15 is a manufacturing process that may be used to manufacture implant systems in accord with another alternative embodiment of the present invention. In the embodiment of FIG. 15, a solution containing SWNT 152 may be sprayed onto an implant 151. After spraying, the SWNTs 152 that remain on the implant, once the carrier (toluene) is flashed off, may be condensed or compacted onto the implant by applying a compressive force to the SWNT 152. This compressive force may be applied by a shrink tube or any other suitable means. The compressive force applied to the SWNT 152 is shown in FIG. 15 by arrows 156.

While various embodiments of the present invention have been described, other embodiments are also plausible. For instance, the implant may be notched or grooved such that therapeutic may be placed therein. These grooves or notches may then be covered with the bucky paper, thereby covering individual vats or channels of therapeutic. Moreover, as discussed above with regard to FIG. 2, the bucky paper may not only cover a device but may also extend past either or both ends of the device.

What is claimed is:

1. A medical implant system comprising:
a medical implant having an exterior surface; and
a first layer of bucky paper covering at least a portion of the exterior surface.

2. The medical implant system of claim 1 wherein the first layer of bucky paper covers the entire exterior surface of the medical implant and the bucky paper contains carbon nanotubes with carboxylic groups positioned on a surface of the carbon nanotubes.

3. The medical implant system of claim 1 wherein the medical implant has a non-continuous exterior surface forming spaces between exterior elements of the medical implant and wherein portions of the first layer of bucky paper have been removed over areas coinciding with at least one space between the exterior elements of the medical implant.

4. The medical implant system of claim 1 wherein the medical implant is a stent.

5. The medical implant system of claim 1 further comprising:
a therapeutic carried by the first layer of bucky paper.

6. The medical implant system of claim 1 wherein therapeutic is positioned between the first layer of bucky paper and the medical implant.

7. The medical implant system of claim 1 further comprising a polymer layer disposed between the first layer of bucky paper and the medical implant, wherein therapeutic is positioned within the polymer layer.

8. The medical implant system of claim 1 wherein therapeutic is placed in a carrier, the carrier positioned in the first layer of bucky paper.

9. The medical implant system of claim 1 further comprising:
a second layer of bucky paper covering at least a portion of the medical implant.

10. The medical implant system of claim 9 further comprising:
a therapeutic positioned between the layers of bucky paper.

11. The medical implant system of claim 10 wherein the therapeutic is contained within a polymer.

12. The medical implant system of claim 1 further comprising:
a therapeutic, the therapeutic carried by the first layer of bucky paper, the therapeutic being in a crystallized state.

13. The medical implant system of claim 1 wherein the bucky paper contains magnetically charged particles.

14. The medical implant system of claim 1 wherein the bucky paper contains anchors extending from the exterior surface, the anchors coupling the first layer of bucky paper to the implant.

15. The medical implant system of claim 9 wherein the first layer of bucky paper contains a first therapeutic and the second layer of bucky paper contains a second therapeutic.

16. The medical implant system of claim 5 wherein the therapeutic is within a carrier.

17. The medical implant system of claim 1 further comprising:
a therapeutic release barrier covering the first layer of bucky paper and a therapeutic.

18. The medical implant system of claim 1 wherein the first layer of bucky paper varies in thickness.

* * * * *

UNITED STATES PATENT AND TRADEMARK OFFICE
CERTIFICATE OF CORRECTION

| | | |
|---|---|---|
| PATENT NO. | : 7,618,647 B2 | Page 1 of 1 |
| APPLICATION NO. | : 10/677834 | |
| DATED | : November 17, 2009 | |
| INVENTOR(S) | : Weber et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1810 days.

Signed and Sealed this

Twenty-sixth Day of October, 2010

David J. Kappos
*Director of the United States Patent and Trademark Office*